US008652451B2

(12) United States Patent
Bui et al.

(10) Patent No.: US 8,652,451 B2
(45) Date of Patent: *Feb. 18, 2014

(54) COMPOSITION COMPRISING A SUGAR SILICONE SURFACTANT AND A OIL-SOLUBLE POLAR MODIFIED POLYMER

(75) Inventors: Hy Si Bui, Piscataway, NJ (US);
Mohamed Kanji, Edison, NJ (US);
Anita Chon Tong, Westfield, NJ (US);
Chunhua Li, Scotch Plains, NJ (US);
Bruno Bavouzet, Hoboken, NJ (US);
Susan Halpern, Paramus, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/825,767

(22) Filed: Jun. 29, 2010

(65) Prior Publication Data
US 2011/0038819 A1    Feb. 17, 2011

Related U.S. Application Data

(60) Provisional application No. 61/221,333, filed on Jun. 29, 2009, provisional application No. 61/221,253, filed on Jun. 29, 2009, provisional application No. 61/221,239, filed on Jun. 29, 2009.

(51) Int. Cl.
*A61Q 1/02* (2006.01)
*A61Q 19/04* (2006.01)
*A61K 8/00* (2006.01)
*A61K 8/18* (2006.01)
*A61Q 5/00* (2006.01)
*A61Q 9/00* (2006.01)

(52) U.S. Cl.
USPC ........................................... 424/63; 424/70.1

(58) Field of Classification Search
USPC ................................................... 424/63, 70.1
See application file for complete search history.

(56) References Cited

U.S. PATENT DOCUMENTS

| 2,957,838 | A | 10/1960 | Mills, Jr. |
| 3,590,076 | A | 6/1971 | Heintzelman et al. |
| 3,699,154 | A | 10/1972 | Heintzelman et al. |
| 3,933,511 | A | 1/1976 | Heintzelman et al. |
| 3,933,512 | A | 1/1976 | Heintzelman et al. |
| 4,041,056 | A | 8/1977 | Heintzelman et al. |
| 4,226,889 | A | 10/1980 | Yuhas |
| 4,420,588 | A | 12/1983 | Yoshioka et al. |
| 4,871,536 | A | 10/1989 | Arraudeau et al. |
| 5,032,391 | A | 7/1991 | Helioff et al. |
| 5,389,363 | A | 2/1995 | Snyder et al. |
| 5,618,524 | A | 4/1997 | Bolich et al. |
| 5,620,693 | A | 4/1997 | Piot et al. |
| 5,800,816 | A | 9/1998 | Brieva et al. |
| 5,911,974 | A | 6/1999 | Brieva et al. |
| 5,965,112 | A | 10/1999 | Brieva et al. |
| 5,985,298 | A | 11/1999 | Brieva et al. |
| 5,998,547 | A * | 12/1999 | Hohner ......................... 525/301 |
| 6,126,929 | A | 10/2000 | Mougin |
| 6,274,152 | B1 | 8/2001 | Brieva et al. |
| 6,464,964 | B1 | 10/2002 | Brieva et al. |
| 6,482,400 | B1 * | 11/2002 | Collin .......................... 424/70.6 |
| 6,492,455 | B1 * | 12/2002 | Nadolsky ....................... 524/559 |
| 6,524,564 | B1 | 2/2003 | Kim et al. |
| 6,562,322 | B2 | 5/2003 | Brieva et al. |
| 6,716,419 | B2 | 4/2004 | Zoltowski et al. |
| 6,780,422 | B2 | 8/2004 | Brieva et al. |
| 6,958,148 | B1 | 10/2005 | Green et al. |
| 7,005,134 | B2 | 2/2006 | Brieva et al. |
| 7,160,550 | B2 | 1/2007 | Brieva et al. |
| 7,186,766 | B2 | 3/2007 | Harashina et al. |
| 7,314,904 | B2 | 1/2008 | Nadolsky et al. |
| 7,423,104 | B2 | 9/2008 | Lion |
| 7,682,621 | B2 | 3/2010 | Lamberty et al. |
| 7,875,265 | B2 | 1/2011 | Blin et al. |
| 8,119,110 | B2 | 2/2012 | Blin et al. |
| 2003/0026816 | A1 | 2/2003 | Zoltowski et al. |
| 2003/0082218 | A1 | 5/2003 | Ichinohe et al. |
| 2003/0147931 | A1 | 8/2003 | Brieva et al. |
| 2003/0182734 | A1 | 10/2003 | Desenne et al. |
| 2004/0170586 | A1 | 9/2004 | Ferrari et al. |
| 2004/0186308 | A1 | 9/2004 | Koch et al. |
| 2004/0223986 | A9 | 11/2004 | Boussouira et al. |
| 2005/0013992 | A1 | 1/2005 | Azad et al. |
| 2005/0180936 | A1 | 8/2005 | Pays |
| 2005/0220728 | A1 | 10/2005 | Kanji et al. |
| 2006/0013840 | A1 | 1/2006 | Lamberty et al. |
| 2006/0084764 | A1 | 4/2006 | Hanna et al. |

(Continued)

FOREIGN PATENT DOCUMENTS

| DE | 100 64 799 | 6/2002 |
| DE | 100 64 799 A1 | 6/2002 |

(Continued)

OTHER PUBLICATIONS

Hauthal, Tenside Surf. Det. 2008, 45 (1), 30-42; published: Jan. 2008.*
U.S. Appl. No. 12/825,707, filed Jun. 29, 2010, Bui, et al.
U.S. Appl. No. 12/825,807, filed Jun. 29, 2010, Bui, et al.
U.S. Appl. No. 12/825,587, filed Jun. 29, 2010, Bui, et al.
U.S. Appl. No. 12/825,840, filed Jun. 29, 2010, Bui, et al.
U.S. Appl. No. 12/825,623, filed Jun. 29, 2010, Bui, et al.
U.S. Appl. No. 12/825,726, filed Jun. 29, 2010, Bui, et al.
U.S. Appl. No. 12/825,633, filed Jun. 29, 2010, Bui, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,730, filed Jun. 29, 2010, Bui, et al.
U.S. Appl. No. 12/825,614, filed Jun. 29, 2010, Bui, et al.
U.S. Appl. No. 12/825,600, filed Jun. 29, 2010, Bui, et al.
U.S. Appl. No. 12/825,559, filed Jun. 29, 2010, Bui, et al.
U.S. Appl. No. 13/133,176, filed Jun. 7, 2011, Bui, et al.
U.S. Appl. No. 13/133,181, filed Aug. 1, 2011, Bui, et al.
U.S. Appl. No. 13/379,691, filed Dec. 21, 2011, Bui et al.

(Continued)

*Primary Examiner* — Gina C Justice
*Assistant Examiner* — Genevieve S Alley
(74) *Attorney, Agent, or Firm* — Oblon, Spivak, McClelland, Maier & Neustadt, L.L.P.

(57) ABSTRACT

The invention relates to a composition comprising a oil-soluble polar modified polymer and a sugar silicone surfactant.

18 Claims, No Drawings

(56) References Cited

U.S. PATENT DOCUMENTS

| | | |
|---|---|---|
| 2006/0093568 A1 | 5/2006 | Blin et al. |
| 2006/0104940 A1 | 5/2006 | Heinrichs et al. |
| 2006/0110345 A1 | 5/2006 | Lu et al. |
| 2006/0115444 A1 | 6/2006 | Blin et al. |
| 2006/0147396 A1 | 7/2006 | Monello |
| 2006/0147402 A1 | 7/2006 | Blin et al. |
| 2006/0159642 A1 | 7/2006 | Hanna et al. |
| 2006/0165626 A1 | 7/2006 | Ricard et al. |
| 2006/0188459 A1 | 8/2006 | Heinrichs et al. |
| 2007/0031361 A1* | 2/2007 | Herrmann et al. ......... 424/70.11 |
| 2007/0092468 A1 | 4/2007 | Brieva et al. |
| 2007/0110700 A1 | 5/2007 | Wells et al. |
| 2007/0110702 A1 | 5/2007 | Ehara |
| 2007/0134181 A1 | 6/2007 | Shimizu et al. |
| 2007/0212315 A1 | 9/2007 | Pastor et al. |
| 2007/0256700 A1 | 11/2007 | Bodelin |
| 2007/0258932 A1 | 11/2007 | Bui et al. |
| 2007/0259012 A1 | 11/2007 | Castro et al. |
| 2008/0025934 A1 | 1/2008 | Lebre et al. |
| 2008/0207871 A1 | 8/2008 | Seiler et al. |
| 2009/0060959 A1 | 3/2009 | Igarashi |
| 2009/0130037 A1 | 5/2009 | Thevenet et al. |
| 2010/0310489 A1 | 12/2010 | Barba |
| 2010/0330012 A1 | 12/2010 | Bui et al. |
| 2010/0330015 A1 | 12/2010 | Bui et al. |
| 2010/0330016 A1 | 12/2010 | Bui et al. |
| 2010/0330017 A1 | 12/2010 | Bui et al. |
| 2010/0330022 A1 | 12/2010 | Bui et al. |
| 2010/0330024 A1 | 12/2010 | Bui et al. |
| 2011/0020254 A1 | 1/2011 | Bui et al. |
| 2011/0020255 A1 | 1/2011 | Bui et al. |
| 2011/0020256 A1 | 1/2011 | Bui et al. |
| 2011/0020257 A1 | 1/2011 | Bui et al. |
| 2011/0020260 A1 | 1/2011 | Bui et al. |
| 2011/0020261 A1 | 1/2011 | Bui et al. |
| 2011/0020263 A1 | 1/2011 | Ilekti et al. |
| 2011/0021681 A1 | 1/2011 | Bui et al. |
| 2011/0021683 A1 | 1/2011 | Bui et al. |
| 2011/0038819 A1 | 2/2011 | Bui et al. |
| 2011/0223122 A1 | 9/2011 | Bui et al. |
| 2011/0223123 A1 | 9/2011 | Bui et al. |
| 2011/0280817 A1 | 11/2011 | Ramadan et al. |
| 2011/0280818 A1 | 11/2011 | Kawaratani et al. |
| 2011/0280820 A1 | 11/2011 | Bui et al. |
| 2011/0286950 A1 | 11/2011 | Bui et al. |
| 2011/0286951 A1 | 11/2011 | Bui et al. |
| 2011/0293550 A1 | 12/2011 | Bui et al. |
| 2011/0311467 A1 | 12/2011 | Bui et al. |
| 2012/0004327 A1 | 1/2012 | Bui et al. |
| 2012/0107263 A1 | 5/2012 | Bui et al. |
| 2012/0171137 A1 | 7/2012 | Bradsaw et al. |
| 2012/0171139 A1 | 7/2012 | Bradshaw et al. |

FOREIGN PATENT DOCUMENTS

| | | | |
|---|---|---|---|
| DE | 102004008941 A1 | | 9/2005 |
| EP | 1 314 415 A1 | | 5/2003 |
| EP | 1 854 451 A2 | | 11/2007 |
| EP | 2 036 536 A1 | | 3/2009 |
| JP | A-07053921 | | 2/1995 |
| WO | WO 96/03967 A1 | | 2/1996 |
| WO | WO 01/17485 | | 3/2001 |
| WO | WO 02/088456 A1 | | 11/2002 |
| WO | WO 02 098379 A1 | | 12/2002 |
| WO | WO 2006/112690 A1 | | 10/2006 |
| WO | WO 2006/127883 | | 11/2006 |
| WO | WO 2006/127883 A2 | | 11/2006 |
| WO | WO/2007/048672 | * | 5/2007 |
| WO | WO 2007/048672 A1 | | 5/2007 |
| WO | WO 2007/096400 A1 | | 8/2007 |
| WO | WO 2007/139812 | | 12/2007 |
| WO | WO 2007/139812 A2 | | 12/2007 |
| WO | WO/2008/046763 | * | 4/2008 |
| WO | WO 2008/046763 | | 4/2008 |
| WO | WO 2008/046763 A1 | | 4/2008 |
| WO | WO 2009/085888 A1 | | 7/2009 |

OTHER PUBLICATIONS

European Office Action Issued Feb. 22, 2013 in Patent Application No. 10 167 788.8.
Hauthal, H. G. Basics, Ingredients, Detergents, Product Safety and Sustainability. Tenside Surf. Det. Jan. 2008, 45 (1), 30-42.
Vertellus, ZeMac(R) E400 Copolymer Technical Data Sheet, May 29, 2008.
European Search Report dated Mar. 10, 2011, in European Application No. 10167784.7.
European Office Action from European Patent Application No. 10167784.7 dated Mar. 21, 2011 (4 pages).
L. Rudnick, Synthesis, Mineral Oils, and Bio-Based Lubricants, Chemistry and Technology.
Perstorp, Boltorn® H20 product data sheet dated Jan. 3, 2008.
Perstorp, Determination of Viscosity for Boltorn Dendritic Polymers, Aug. 23, 2011.
Mulkern et al. Polymer, 2000, 41 (9), 3193-3203.
Bergbreiter et al. Tetrahedron Letters, 1997, 38 (21), 3703-3706.
European Search Report issued Apr. 8, 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.
International Search Report issued Jul. 23, 2010 in PCT/US09/68245 filed Dec. 16, 2009.
Extended European Search Report Issued Nov. 29, 2012 in Patent Application No. 08867867.7.
International Search Report issued May 31, 2010 in PCT/US09/067338 filed Dec. 9, 2009.

* cited by examiner

COMPOSITION COMPRISING A SUGAR SILICONE SURFACTANT AND A OIL-SOLUBLE POLAR MODIFIED POLYMER

CROSS-REFERENCE TO RELATED APPLICATIONS

This application claims the benefit of priority from U.S. Provisional Application Ser. Nos. 61/221,239, 61/221,253, and 61/221,333, all filed on Jun. 29, 2009, the entire contents of which are hereby incorporated by reference.

FIELD OF THE INVENTION

The present invention relates to a composition comprising at least one sugar silicone surfactant and at least one Oil-soluble polar modified polymer. Such compositions have industrial, pharmacological and/or cosmetic applicability.

DISCUSSION OF THE BACKGROUND

U.S. Pat. No. 6,492,455 discloses water-soluble reaction products of polyamines and C6 olefin/maleic anhydride copolymers. Because these compositions are water-soluble, addition of water to such reaction products renders the products unsuitable for applications requiring water-insolubility. For example, such reaction products are unsuitable for use as a solid carrier containing colorant (for example, industrial pigments) or active agents (for example, pharmaceuticals) because the reaction product breaks down upon exposure to water.

Thus, there remains a need for improved products which can function as a carrier and/or matrix for desired agents.

Further, a problem with conventional lip make up products is their inability to continuously hydrate and moisturize the lips. The reason for this is that water either has to be deposited onto the lips from the gloss itself or drawn to the lips from the atmosphere. In the event that the source of water for hydration is the product itself, it is very difficult to maintain the water in a stabilized form. Failure to do so results in the water quickly evaporating from the surface of the lips leaving the lips feeling dry.

Also, conventional lip compositions which impart a high degree of gloss onto the lip surface require the presence of silicone fluids in the composition. Silicone fluids are known to have high refractive indices which provide shine. These types of silicone fluids, however, have poor environmental profiles and are relatively expensive.

Therefore, it is desirable to provide lip compositions, having a high degree of gloss, which are capable of hydrating and/or moisturizing the lips in a continuous manner.

SUMMARY OF THE INVENTION

The present invention relates to a composition comprising at least one sugar silicone surfactant and at least one oil-soluble polar modified polymer.

The present invention also relates to compositions comprising at least one sugar silicone surfactant, at least one oil-soluble polar modified polymer, and a desired agent such as a colorant or pharmacologically active agent.

The present invention also relates to compositions, preferably solid compositions, comprising at least one sugar silicone surfactant, at least one oil-soluble polar modified polymer, and water. Preferably, such compositions further comprise a desired agent.

The present invention also relates to compositions, preferably solid compositions, comprising at least one sugar silicone surfactant, at least one oil-soluble polar modified polymer, and at least one oil. Preferably, such compositions further comprise a desired agent.

The present invention also relates to methods of treating, caring for and/or making up keratinous material (for example, skin, eyes, eyelashes or lips) by applying cosmetic compositions of the present invention to the keratinous material in an amount sufficient to treat, care for and/or make up the keratinous material.

The present invention also relates to methods of improving the feel or texture properties of a cosmetic composition upon application to a keratin material, comprising forming a composition comprising at least one sugar silicone surfactant and at least one oil-soluble polar modified polymer.

The present invention also relates to methods of applying the above-disclosed compositions onto keratinous materials such as skin or lips in an amount sufficient to make up, provide color, and/or provide hydration or moisturization to the keratinous materials. It has been surprisingly found that compositions, according to an embodiment of the present invention impart non-sticky hydration and moisturization to the keratinous materials.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

In accordance with the present invention, the "hardness" of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf, including all ranges and subranges therebetween.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettle: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil soluble polar modified polymer(s) represent from about 1% to about 30% of the total weight of the composition, more preferably from about 2.5% to about 15% of the total weight of the composition, and most preferably from about 5% to about 10%, including all ranges and subranges therebetween.

Sugar Silicone Surfactant

According to the present invention, compositions comprising at least one sugar silicone surfactant are provided. The sugar silicone surfactant of the present invention has the following formula:

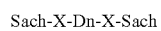

where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosylsucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula R2SiO, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, lactobionolactonesiloxane, or a mixture thereof.

Preferably, the sugar silicone surfactant represents from about 0.5% to about 25% of the total weight of the composition, more preferably from about 0.75% to about 15% of the total weight of the composition, and most preferably from about 1% to about 10%, including all ranges and subranges therebetween.

Alkoxylated Surfactant

According to preferred embodiments of the present invention, compositions of the present invention may further comprise at least one alkoxylated surfactant having at least 8 carbon atoms and at least two alkoxylation units. Preferably, the alkoxylated surfactant comprises 8 to 30 carbon atoms, more preferably 8 to 22 carbon atoms, and most preferably 10 to 16 carbon atoms. Also preferably, the alkoxylated surfactants comprise 2 to 100 alkoxylation units, more preferably 10 to 50 alkoxylation units, and most preferably 20 to 50 alkoxylation units. Suitable alkoxylated surfactants are well known in the art and comprise fatty potions (for example, cetyl, stearyl, oleyl, synthetic fatty alcohols, etc.) in combination with alkoxylation units (for example, ethoxylation and propoxylation). Specific examples include, but are not limited to, steareth surfactants (for example, steareth-21), ceteth surfactants, oleth surfactants, pareth surfactants and the like. A particularly preferred surfactant is C11-C15 Pareth-40.

Preferably, the alkoxylated surfactant having at least 8 carbon atoms and at least two alkoxylation units represents from about 0.5% to about 20% of the total weight of the composition, more preferably from about 0.75% to about 15% of the total weight of the composition, and most preferably from about 1% to about 10%, including all ranges and subranges therebetween.

Alcohol

According to the preferred embodiments of the present invention, compositions of the present invention may further comprise at least one alcohol. The alcohol may be either liner or branched. Preferably, the alcohol is non-volatile, having an elevated boiling point. For example, the alcohol has a boiling point of at least 50° C., 75° C., or 100° C. Also preferably, the alcohol has at least 8 carbon atoms, preferably at least 10 carbon atoms. Suitable examples of acceptable alcohols include butyl octanol, butyl nonanol, butyl decanol, pentyl octanol, pentyl nonanol, pentyl decanol, hexyl octanol, hexyl nonanol, and hexyl decanol.

Preferably, the alcohol(s) represent from about 0.1% to about 30% of the total weight of the composition, more preferably from about 0.5% to about 15% of the total weight of the composition, and most preferably from about 1% to about 10%, including all ranges and subranges therebetween.

According to particularly preferred embodiments of the present invention, the alcohol, the alkoxylated surfactant having at least 8 carbon atoms and at least two alkoxylation units, and the sugar silicone surfactant are combined to form an emulsion. A suitable example of such an emulsion is the product sold by Dow Corning under the designation CE-8810 (gluconamidoethylaminopropylsilicone/C11-C15 Pareth-40/butyloctanol).

According to preferred embodiments, the composition may further comprise volatile and/or non-volatile oils. Such oils can be any acceptable oil including but not limited to silicone oils and/or hydrocarbon oils.

According to preferred embodiments, the composition may further comprise one or more volatile silicone oils. Examples of such volatile silicone oils include linear or cyclic silicone oils having a viscosity at room temperature less than or equal to 6cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the composition may further comprise one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to preferred embodiments of the present invention, the composition may further comprise at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments of the present invention, a desired agent can be incorporated within the composition. The desired agent can be, for example, any colorant (pigment, dye, etc.), any pharmaceutically or cosmetically active agent, or any film forming agent known in the art. Such a desired agent can be incorporated into the composition of the present invention and can be active during subsequent use of the composition. For example, a cosmetic makeup composition or a paint composition comprising colorant can provide colorant and/or filim forming agent to a substrate (skin, lips, wall, frame, etc.) during use to provide the substrate with the desired film and/or color. Similarly, a pharmaceutical or cosmetic composition comprising a pharmaceutically active agent can provide such active agent to the patient or consumer upon use (for example, a transdermal patch within which is a pharmaceutically or cosmetically active agent, or a tablet or capsule containing the active agent).

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

According to preferred embodiments of the present invention, compositions of the present invention can comprise substantial amounts of water. Preferably, compositions of the present invention comprise from about 5% to about 50% water, more preferably from about 15% to about 45% water, and more preferably from about 25% to about 40% water by weight with respect to the total weight of the composition, including all ranges and subranges therebetween. According to particularly preferred embodiments, compositions of the present invention and at least 25% water are solid compositions. Such solid compositions are preferably in the form of a stick (for example, a lipstick or a stick foundation).

Compositions of the present invention can optionally further comprise any additive usually used in the field(s) under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

Another particularly preferred embodiment of the present invention is a composition which contains so little elastomer that the presence of such elastomer not affect the cosmetic properties of the composition. Preferably, the compositions are substantially free of such elastomers (i.e., contain less than about 0.5% elastomer), essentially free of such elastomers (i.e., contain less than about 0.25% elastomer) or free of such elastomer (i.e., contain no elastomer).

According to other embodiments of the present invention, the compositions of the present invention are anhydrous. By "anhydrous," it is meant that the composition contains substantially no water (that is, less than about 5% by weight of the composition of water).

According to other preferred embodiments, methods of treating, caring for and/or enhancing the appearance of keratinous material by applying compositions of the present invention to the keratinous material in an amount sufficient to treat, care for and/or enhance the appearance of the keratinous material are provided. In accordance with these preceding preferred embodiments, the compositions of the present invention comprising at least one polar modified wax and at least one sugar silicone surfactant are applied topically to the desired area of the keratin material in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved feel upon application (for example, texture, reduced drag or tackiness), and/or increased shine/color characteristics are provided.

According to other embodiments of the present invention, methods of improving the hydration, feel upon application, shine/color and/or moisturization properties of a composition, comprising adding at least one oil-soluble polar modified polymer and at least one sugar silicone surfactant to the composition are provided. In accordance with this embodiment, the at least one oil-soluble polar modified polymer and the at least one sugar silicone surfactant are present in amounts sufficient to achieve the desired result.

According to other embodiments of the present invention, methods of moisturizing or hydrating keratinous material such as lips or skin by applying the compositions of the present invention to the keratinous material are provided. It has surprisingly been discovered that the association of a sugar silicone surfactant with the above-described polar modified polymer results in the formation of a stable emulsion capable of imparting high gloss onto the lips, in the absence of any conventional silicone fluids used to provide shine. Moreover, the use of the sugar silicone surfactant eliminates the need for using surfactant/emulsifiers to form the stable emulsion. Finally, the resultant composition, when applied onto the lips, both hydrates and moisturizes the lips or skin dues to the large amount of water entrapped therein, while at the same time making the lips or skin feel unusually refreshed and pleasant.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Mascara Composition

| Phase | Chemical Name | Weight % |
|---|---|---|
| A | Caprylic/capric Triglyceride | 1.00 |
| A | Oil-soluble polar modified polymer | 9.33 |
| A | Iron Oxides | 8.00 |
| A | Isododecane | 30.92 |
| A | Propylparaben | 0.20 |
| B | DI Water | 25.00 |
| B | Disodium EDTA | 0.10 |
| B | Potassium Cetyl Phosphate | 2.00 |
| B | Methylparaben | 0.25 |
| B | Pentylene Glycol | 2.00 |
| B | Sugar silicone surfactant | 20.00 |
| C | Simethicone | 0.10 |

-continued

| Phase | Chemical Name | Weight % |
|---|---|---|
| D | PHENOXYETHANOL (and) METHYLPARABEN (and) ISOPROPYLPARABEN (and) ISOBUTYLPARABEN (and) BUTYLPARABEN | 1.10 |

Procedure

1. In a suitable size metal container, added Caprylic/capric Triglyceride, PPMA and propylparaben. Heated contents to 90 C or until all solids had melted.
2. When all solids had melted, Isododecane was added to batch.
3. Added iron oxide and started homogenizing batch for at least 1 hr.
4. In side tank B with water bath, added all phase B and mixed until uniform. Heated contents to 90 C.
5. Mix side tank B for 20 minutes.
6. When both tanks were at temperature, slowly added side tank B to main tank A while homogenizing at 850 rpm.
7. After 5 minutes of homogenizing, added Simethicone.
8. Homogenized for 30 minutes at 90 C.
9. Batch was cooled naturally to 25 C.
10. Phase D was added to container A at 35 C and was furthered cooled to 25 C.
11. The contents were poured into appropriate containers.

EXAMPLE 1

Lip Stick Composition

| Phase | Chemical Name | Weight % |
|---|---|---|
| A | Polyglyceryl-2 Triisosterate | 3.00 |
| A | Octyldodecyl Neopantanoate | 14.18 |
| A | Hydrogenated Polydecene | Q.S. |
| A | Polyethylene 400 | 8.00 |
| A | Oil-soluble polar modified polymer | 7.00 |
| A | Tricaprylin | 13.80 |
| B | Color pigments | 5.00 |
| B | Mica | 2.00 |
| C | Deionized Water | 17.50 |
| C | Glycerin | 3.00 |
| C | Sugar silicone surfactant | 10.00 |

Procedure

1. Phase A materials were added to a suitable size beaker A and heated to 95 Celsius degrees.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker B, glycerin, and sugar silicone surfactant were added into DI water and mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes.
7. The contents were poured into lipstick molds at 80 Celsius degrees.
8. The lipstick in molds was placed in a cooling tunnel for 15 minutes at −10 Celsius degrees. Once cooled, the lipstick in molds were removed from the cooling tunnel to equilibrate to 25 Celsius degrees and removed from the molds after lipsticks had thawed to 25 Celsius degrees.

EXAMPLE 2

Lip gloss Composition

| Phase | Chemical Name | Ex 2 |
|---|---|---|
| A | Polyglyceryl-2 Triisosterate | 6.00 |
| A | Octyldodecyl Neopantanoate | 5.93 |
| A | Hydrogenated Polydecene | Q.S. |
| A | Oil-soluble polar modified polymer | 10.00 |
| A | Tricaprylin | 13.80 |
| B | Color pigments | 5.00 |
| B | Mica | 2.00 |
| C | Deionized Water | 35.00 |
| C | Glycerin | 3.00 |
| C | Sugar silicone Surfactant | 10.00 |

Procedure

1. Phase A materials were added to a suitable size beaker A and heated to 95 Celsius degrees.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker B, glycerin and sugar silicone surfactant were added into DI water and mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes until contents were cooled to 25 Celsius degrees.
7. The contents of main beaker A was poured into container.

EXAMPLE 4

Foundation Composition

| | Chemical Name | Weight % |
|---|---|---|
| A | isododecane | Q.S. |
| | isohexadecane | 2.25 |
| | Oil-soluble polar modified polymer | 6.75 |
| | Pigment | 10 |
| | polyglyceryl-2-triisostearate | 2.5 |
| B | DI Water | 21 |
| | cellulose | 0.2 |

-continued

| Chemical Name | Weight % |
|---|---|
| sugar silicone surfactant | 15 |
| Preservatives | 1.50 |
| Total | 100 |

Procedure

1. In container A, Oil-soluble polar modified polymer was melted in the isohexadecane and isododecane until fully dissolved. The temperature was brought to 90° C.

2. While maintaining the temperature, polyglyceryl-2-triisostearate and pigment were added to container A until fully dissolved.

3. In a separate container B, water, cellulose, sugar silicone surfactant and preservatives were mixed and heated to 900 C.

4. The contents of container B were added to the contents of container A slowly at high sheer (~1000 rpm).

5. Heat was maintained at 70° C.-80° C. for 20 minutes while maintaining high sheer mixing.

6. The mixture was cooled to room temperature while mixing.

EXAMPLE 5

A cosmetic composition was prepared containing the below-disclosed ingredients.

| | |
|---|---|
| isohexadecane | 2.25 |
| isododecane | 38.85 |
| PP207* | 6.75 |
| polyglyceryl-2 triisostearate | 2.50 |
| DI Water | 23.00 |
| cellulose | 0.15 |
| sugar silicone surfactant (40% water) | 15.00 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.40 |
| CHLORPHENESIN | 0.20 |
| ETHYL PARABEN | 0.20 |
| TOTAL | 100.00 |

*PP207 is a linear polypropylene-ethylene-maleic anhydride copolymer wax commercially available from Clariant under the tradename LICOCARE PP207 LP 3349.

Procedure

1. In container A, PP207 was melted in the isohexadecane and isododecane until fully dissolved. The temperature was brought to 90° C.

2. While maintaining the temperature, the emulsifier and pigment grind were added to container A until fully dissolved.

3. In a separate container B, sugar silicone surfactant, water, cellulose, and preservatives were mixed at room temperature.

4. The contents of container B were added to the contents of container A slowly at high sheer (~700 rpm).

5. Heat was maintained at 70° C.-80° C. for 20 minutes while maintaining high sheer mixing.

6. The mixture was cooled to room temperature while mixing.

EXAMPLE 6

| Phase | Chemical Name | Example 6 |
|---|---|---|
| A | Non-volatile Solvent | Q.S. |
| A | Polyethylene 400 | 8.00 |
| A | Polypropylene-ethylene-maleic anhydride copolymer wax | 7.00 |
| A | Pigment | 3.50 |
| A | Mica | 2.00 |
| B | Deionized Water | 22.50 |
| B | Glycerin | 3.00 |
| B | Sugar Silicone Surfactant | 10.00 |
| | Total | 100.00 |

Procedure:

1. The following were added to a suitable size beaker A and heated to 95 Celsius degrees: non-volatile solvent, polyethylene 400, polyprophylene-theylene-maleic anhydride copolymer wax.

2. When enough solids had melted, the contents were mixed with moderate speed until all solids had melted at 95 Celsius degrees.

3. The temperature was slightly lowered to 85 Celsius degrees and pigments and mica were added.

4. The contents of main beaker A was transferred to a Silverson mixer for emulsification while maintaining the temperature at 85-90 Celsius degrees.

5. In a separate beaker 2, glycerin and Sugar Silicone Surfactant were added into DI water and mixed and heated to 85 Celsius degrees.

6. The contents of side beaker B was added dropwise into the beaker A while emulsifying at 9000 rpm under the Silverson mixer for 30 minutes. Afterward, the emulsification speed was lowered to 2000 rpm for 5 minutes.

7. The contents were poured into lipstick molds at 80 Celsius degrees.

8. The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 7

| Phase | Chemical Name | Example 7 |
|---|---|---|
| A | Non-volatile Solvent | Q.S. |
| A | Polypropylene-ethylene-maleic anhydride copolymer wax | 10.00 |
| A | Pigment | 3.50 |
| A | Mica | 2.00 |
| B | Deionized Water | 40.00 |
| B | Glycerin | 3.00 |
| B | Sugar Silicone Surfactant | 10.00 |
| | Total | 100.00 |

Procedure:

1. The following were added to a suitable size beaker A and heated to 95 Celsius degrees: non-volatile solvent, polyprophylene-theylene-maleic anhydride copolymer wax.

2. When enough solids had melted, the contents were mixed with moderate speed until all solids had melted at 95 Celsius degrees.

3. The temperature was slightly lowered to 85 Celsius degrees and pigments and mica were added.

4. The contents of main beaker A was transferred to a Silverson mixer for emulsification while maintaining the temperature at 85-90 Celsius degrees.

5. In a separate beaker 2, glycerin and Sugar Silicone Surfactant were added into DI water and mixed and heated to 85 Celsius degrees.

6. The contents of side beaker B was added dropwise into the beaker A while emulsifying at 9000 rpm under the Silverson mixer for 30 minutes. Afterward, the emulsification speed was lowered to 2000 rpm for 5 minutes until contents were cooled to 25 Celsius degrees.

7. The contents of main beaker A was poured into container.

What is claimed is:

1. A composition comprising:
   (a) water;
   (b) at least one oil-soluble polar modified polymer consisting of polypropylene and/or polyetheylene monomers, and maleic anhydride units, and having a weight-average molecular weight of less than or equal to 25 000 g/mol and a melting point above 75° C.; and
   (c) a surfactant system comprising at least one sugar silicone surfactant,
   wherein the composition is in the form of an emulsion.

2. The composition of claim 1, wherein the sugar silicone surfactant is gluconamidoethylaminopropylsilicone.

3. The composition of claim 1, wherein the sugar silicone surfactant is present in an amount of from about 0.5% to about 25% by weight, based on the weight of the composition.

4. The composition of claim 1, wherein the oil-soluble polar modified polymer is present in an amount of from about 1% to about 30% by weight, based on the weight of the composition.

5. The composition of claim 1, wherein water is present in an amount of from about 5% to about 50% by weight, based on the weight of the composition.

6. The composition of claim 1, further comprising at least one non-volatile solvent.

7. The composition of claim 6, wherein the non-volatile solvent is present in an amount of from about 0.5% to about 15% by weight, based on the weight of the composition.

8. The composition of claim 1, further comprising at least one volatile solvent present in an amount of from about 5% to about 80% by weight, based on the weight of the composition.

9. The composition of claim 1, further comprising at least one colorant.

10. A method of making-up a keratinous material comprising applying onto the keratinous material the composition according to claim 1 in an amount sufficient to make-up the keratinous material.

11. The method of claim 10, wherein the keratinous material is skin.

12. The method of claim 10, wherein the keratinous material is lips.

13. The composition of claim 1, wherein the weight-average molecular weight of the oil-soluble polar modified polymer is from 1,000 g/mol to 22,000 g/mol.

14. The composition of claim 1, wherein the melting point of the oil-soluble polar modified polymer is between 90° C. and 160° C.

15. The composition of claim 1, wherein the oil-soluble polar modified polymer has from about 0.5% to about 10% maleic anhydride units by weight with respect to the weight of the oil soluble polar modified polymer.

16. The composition of claim 1, wherein the oil-soluble polar modified polymer has from about 1% to about 8% maleic anhydride units by weight with respect to the weight of the oil soluble polar modified polymer.

17. The composition of claim 1, wherein the emulsion is in the form of a mascara, a lipstick, a lip gloss, or a foundation.

18. The composition of claim 1, wherein the surfactant system consists essentially of the at least one silicone sugar surfactant.

* * * * *